(12) United States Patent
Moretti et al.

(10) Patent No.: US 11,278,272 B2
(45) Date of Patent: Mar. 22, 2022

(54) ENDOSCOPIC SUTURING NEEDLE AND SUTURE ASSEMBLY ATTACHMENT METHODS

(71) Applicant: BOSTON SCIENTIFIC SCIMED, INC., Maple Grove, MN (US)

(72) Inventors: Briana J. Moretti, Franklin, MA (US); Ashrita Raghuram, Brighton, MA (US); Shaun D. Comee, Fiskdale, MA (US); Christopher R. Deuel, Melrose, MA (US); Stan Gilbert, Litchfield, NH (US); Thomas Jones, Milford, MA (US); Kevin Windheuser, Hopkinton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 165 days.

(21) Appl. No.: 16/561,933

(22) Filed: Sep. 5, 2019

(65) Prior Publication Data
US 2020/0078006 A1 Mar. 12, 2020

Related U.S. Application Data

(60) Provisional application No. 62/848,885, filed on May 16, 2019, provisional application No. 62/727,783, filed on Sep. 6, 2018.

(51) Int. Cl.
A61B 17/04 (2006.01)
A61B 17/06 (2006.01)
A61B 17/00 (2006.01)

(52) U.S. Cl.
CPC ...... *A61B 17/0469* (2013.01); *A61B 17/0482* (2013.01); *A61B 17/06066* (2013.01);
(Continued)

(58) Field of Classification Search
CPC . A61B 17/06; A61B 17/0469; A61B 17/0482; A61B 17/06006;
(Continued)

(56) References Cited

U.S. PATENT DOCUMENTS 5,478,344 A 12/1995 Stone
5,584,861 A 12/1996 Swain et al.
(Continued)

FOREIGN PATENT DOCUMENTS

CA 2682488 A1 10/2008
DE 202005022017 U1 5/2012
(Continued)

OTHER PUBLICATIONS

International Search Report and Written Opinion dated Aug. 20, 2019 for International Application No. PCT/US2019/033748.
(Continued)

*Primary Examiner* — Tuan V Nguyen
(74) *Attorney, Agent, or Firm* — Seager, Tufte & Wickhem, LLP

(57) ABSTRACT

A suture assembly may include a needle having a cylindrical body with a sharp point on at least one end, a lumen extending transverse to a longitudinal axis of the cylindrical body, and a recess in communication with an opening to the lumen. A suture extends through the lumen and is secured within the recess of the needle by a sleeve extending over the needle.

14 Claims, 19 Drawing Sheets

(52) U.S. Cl.
CPC .............. *A61B 2017/00477* (2013.01); *A61B 2017/0474* (2013.01); *A61B 2017/061* (2013.01); *A61B 2017/0609* (2013.01); *A61B 2017/06038* (2013.01); *A61B 2017/06047* (2013.01)

(58) Field of Classification Search
CPC ...... A61B 17/06004; A61B 2017/0472; A61B 2017/0609; A61B 2017/06047
See application file for complete search history.

(56) References Cited

U.S. PATENT DOCUMENTS

| | | | |
|---|---|---|---|
| 5,674,229 A * | 10/1997 | Tovey | A61B 17/0469 606/139 |
| 6,086,608 A | 7/2000 | Ek et al. | |
| 6,200,329 B1 | 3/2001 | Fung et al. | |
| 6,494,888 B1 | 12/2002 | Laufer et al. | |
| 6,506,196 B1 | 1/2003 | Laufer | |
| 6,554,845 B1 | 4/2003 | Fleenor et al. | |
| 6,569,085 B2 | 5/2003 | Kortenbach et al. | |
| 6,626,917 B1 | 9/2003 | Craig | |
| 6,663,639 B1 | 12/2003 | Laufer et al. | |
| 6,719,763 B2 | 4/2004 | Chung et al. | |
| 6,740,030 B2 | 5/2004 | Martone et al. | |
| 6,746,457 B2 | 6/2004 | Dana et al. | |
| 6,755,843 B2 | 6/2004 | Chung et al. | |
| 6,773,441 B1 | 8/2004 | Laufer et al. | |
| 6,808,491 B2 | 10/2004 | Kortenbach et al. | |
| 6,821,285 B2 | 11/2004 | Laufer et al. | |
| 6,835,200 B2 | 12/2004 | Laufer et al. | |
| 6,908,427 B2 | 6/2005 | Fleener et al. | |
| 6,997,931 B2 | 2/2006 | Sauer et al. | |
| 7,056,284 B2 | 6/2006 | Martone et al. | |
| 7,063,710 B2 | 6/2006 | Takamoto et al. | |
| 7,063,715 B2 | 6/2006 | Onuki et al. | |
| 7,094,246 B2 | 8/2006 | Anderson et al. | |
| 7,144,401 B2 | 12/2006 | Yamamoto et al. | |
| 7,147,646 B2 | 12/2006 | Dana et al. | |
| 7,153,314 B2 | 12/2006 | Laufer et al. | |
| 7,220,266 B2 | 5/2007 | Gambale | |
| 7,232,445 B2 | 6/2007 | Kortenbach et al. | |
| 7,235,086 B2 | 6/2007 | Sauer et al. | |
| 7,326,221 B2 | 2/2008 | Sakamoto et al. | |
| 7,344,545 B2 | 3/2008 | Takemoto et al. | |
| 7,347,863 B2 | 3/2008 | Rothe et al. | |
| 7,361,180 B2 | 4/2008 | Saadat et al. | |
| 7,530,985 B2 | 5/2009 | Takemoto et al. | |
| 7,601,161 B1 | 10/2009 | Nobles et al. | |
| 7,618,425 B2 | 11/2009 | Yamamoto et al. | |
| 7,713,277 B2 | 5/2010 | Laufer et al. | |
| 7,722,633 B2 | 5/2010 | Laufer et al. | |
| 7,727,246 B2 | 6/2010 | Sixto, Jr. et al. | |
| 7,736,373 B2 | 6/2010 | Laufer et al. | |
| 7,776,057 B2 | 8/2010 | Laufer et al. | |
| 7,776,066 B2 | 8/2010 | Onuki et al. | |
| 7,842,051 B2 | 11/2010 | Dana et al. | |
| 7,846,180 B2 | 12/2010 | Cerier | |
| 7,857,823 B2 | 12/2010 | Laufer et al. | |
| 7,896,893 B2 | 3/2011 | Laufer et al. | |
| 7,918,867 B2 | 4/2011 | Dana et al. | |
| 7,951,157 B2 | 5/2011 | Gambale | |
| 7,992,571 B2 | 8/2011 | Gross et al. | |
| 7,993,368 B2 | 8/2011 | Gambale et al. | |
| 8,016,840 B2 | 9/2011 | Takemoto et al. | |
| 8,021,376 B2 | 9/2011 | Takemoto et al. | |
| 8,057,494 B2 | 11/2011 | Laufer et al. | |
| 8,062,314 B2 | 11/2011 | Sixto, Jr. et al. | |
| 8,066,721 B2 | 11/2011 | Kortenbach et al. | |
| 8,105,355 B2 | 1/2012 | Page et al. | |
| 8,211,123 B2 | 7/2012 | Gross et al. | |
| 8,216,253 B2 | 7/2012 | Saadat et al. | |
| 8,226,667 B2 | 7/2012 | Viola et al. | |
| 8,277,468 B2 | 10/2012 | Laufer et al. | |
| 8,287,554 B2 | 10/2012 | Cerier et al. | |
| 8,287,556 B2 | 10/2012 | Gilkey et al. | |
| 8,308,765 B2 | 11/2012 | Saadat et al. | |
| 8,313,496 B2 | 11/2012 | Sauer et al. | |
| 8,361,089 B2 | 1/2013 | Chu | |
| 8,388,632 B2 | 3/2013 | Gambale | |
| 8,425,555 B2 | 4/2013 | Page et al. | |
| 8,454,631 B2 | 6/2013 | Viola et al. | |
| 8,480,691 B2 | 7/2013 | Dana et al. | |
| 8,540,735 B2 | 9/2013 | Mitelberg et al. | |
| 8,551,120 B2 | 10/2013 | Gambale | |
| 8,585,720 B2 | 11/2013 | Gross et al. | |
| 8,632,553 B2 | 1/2014 | Sakamoto et al. | |
| 8,679,136 B2 | 3/2014 | Mitelberg | |
| 8,709,022 B2 | 4/2014 | Stone et al. | |
| 8,764,771 B2 | 7/2014 | Chu | |
| 8,882,785 B2 | 11/2014 | DiCesare et al. | |
| 8,926,634 B2 | 1/2015 | Rothe et al. | |
| 8,992,570 B2 | 3/2015 | Gambale et al. | |
| 9,011,466 B2 | 4/2015 | Adams et al. | |
| 9,089,325 B2 | 7/2015 | Mitelberg et al. | |
| 9,125,646 B2 | 9/2015 | Woodard, Jr. et al. | |
| 9,198,562 B2 | 12/2015 | Mitelberg et al. | |
| 9,320,515 B2 | 4/2016 | Dana et al. | |
| 9,486,126 B2 | 11/2016 | West et al. | |
| 9,504,465 B2 | 11/2016 | Chu | |
| 9,510,817 B2 | 11/2016 | Saadat et al. | |
| 9,549,728 B2 | 1/2017 | Chu | |
| 9,750,494 B2 | 9/2017 | Gross et al. | |
| 9,788,831 B2 | 10/2017 | Mitelberg | |
| 9,844,366 B2 | 12/2017 | Woodard, Jr. et al. | |
| 9,867,610 B2 | 1/2018 | Mitelberg et al. | |
| 10,045,871 B2 | 8/2018 | Saadat et al. | |
| 10,143,463 B2 | 12/2018 | Dana et al. | |
| 10,194,902 B2 | 2/2019 | Nobles et al. | |
| 10,335,142 B2 | 7/2019 | Raybin et al. | |
| 2002/0107530 A1 | 8/2002 | Sauer et al. | |
| 2003/0204205 A1 | 10/2003 | Sauer et al. | |
| 2004/0002699 A1 | 1/2004 | Ryan et al. | |
| 2004/0138706 A1 | 7/2004 | Abrams et al. | |
| 2005/0033319 A1 | 2/2005 | Gambale et al. | |
| 2005/0250985 A1 | 11/2005 | Saadat et al. | |
| 2006/0282094 A1 | 12/2006 | Stokes et al. | |
| 2007/0270908 A1 | 11/2007 | Stokes et al. | |
| 2008/0086148 A1 | 4/2008 | Baker et al. | |
| 2009/0177031 A1 | 7/2009 | Surti et al. | |
| 2010/0137681 A1 | 6/2010 | Ewers et al. | |
| 2010/0198006 A1 | 8/2010 | Greenburg et al. | |
| 2012/0158023 A1 | 6/2012 | Miltelberg et al. | |
| 2012/0271327 A1 | 10/2012 | West et al. | |
| 2013/0096581 A1 | 4/2013 | Gilkey et al. | |
| 2013/0096583 A1* | 4/2013 | Mueller | A61B 90/30 606/148 |
| 2013/0304093 A1 | 11/2013 | Serina et al. | |
| 2014/0121457 A1 | 5/2014 | Mort et al. | |
| 2014/0128668 A1 | 5/2014 | Cox et al. | |
| 2015/0126983 A1 | 5/2015 | Alvarado et al. | |
| 2016/0045197 A1 | 2/2016 | Mitelberg et al. | |
| 2017/0042534 A1 | 2/2017 | Nobles et al. | |
| 2017/0086817 A1 | 3/2017 | Mitelberg | |
| 2017/0086818 A1 | 3/2017 | Mitelberg | |
| 2017/0119371 A1 | 5/2017 | Mims et al. | |
| 2017/0319197 A1 | 11/2017 | Gross et al. | |
| 2018/0042602 A1 | 2/2018 | Mitelberg et al. | |
| 2018/0042603 A1 | 2/2018 | Mitelberg et al. | |
| 2018/0153381 A1 | 6/2018 | Wei et al. | |
| 2018/0221009 A1 | 8/2018 | Mitelberg et al. | |
| 2018/0235604 A1 | 8/2018 | Comee et al. | |
| 2018/0344501 A1 | 12/2018 | Saadat et al. | |

FOREIGN PATENT DOCUMENTS

| | | |
|---|---|---|
| EP | 1520509 A1 | 4/2005 |
| EP | 2108304 A2 | 10/2009 |
| WO | 0189393 A1 | 11/2001 |
| WO | 2008016592 A2 | 2/2008 |
| WO | 2008045376 A2 | 4/2008 |
| WO | 2008098124 A1 | 8/2008 |
| WO | 2010036227 A1 | 4/2010 |

(56) References Cited

FOREIGN PATENT DOCUMENTS

| WO | 2016200811 A1 | 12/2016 |
| WO | 2017087856 A1 | 5/2017 |
| WO | 2018156603 A1 | 8/2018 |

OTHER PUBLICATIONS

International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
International Search Report and Written Opinion dated Sep. 20, 2019 for International Application No. PCT/US2019/039312.
International Search Report and Written Opinion dated Nov. 18, 2019 for International Application No. PCT/US2019/049774.

\* cited by examiner

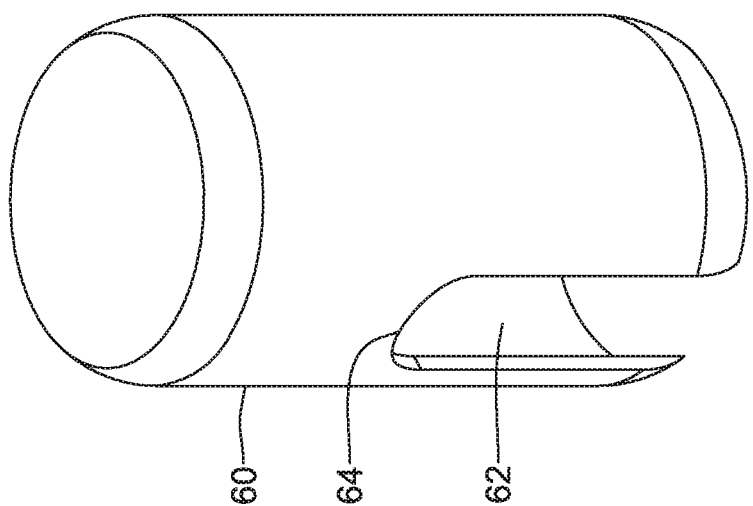

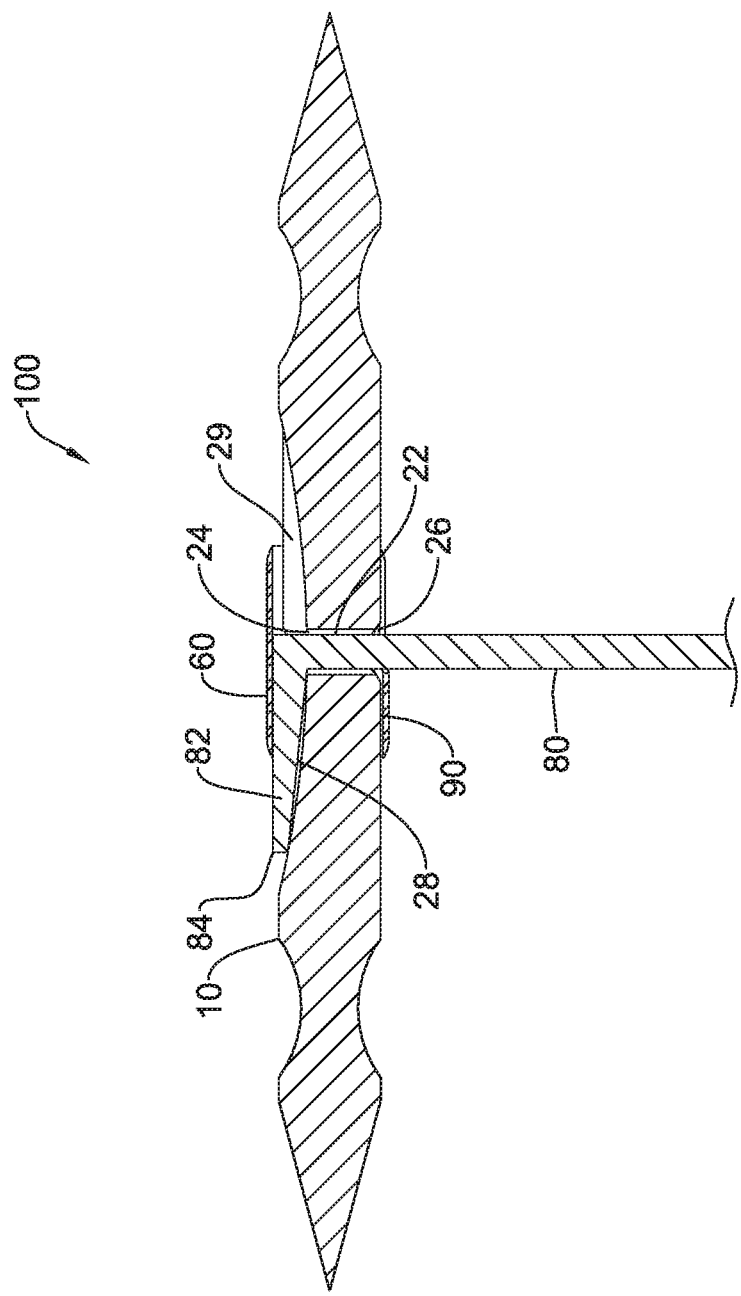

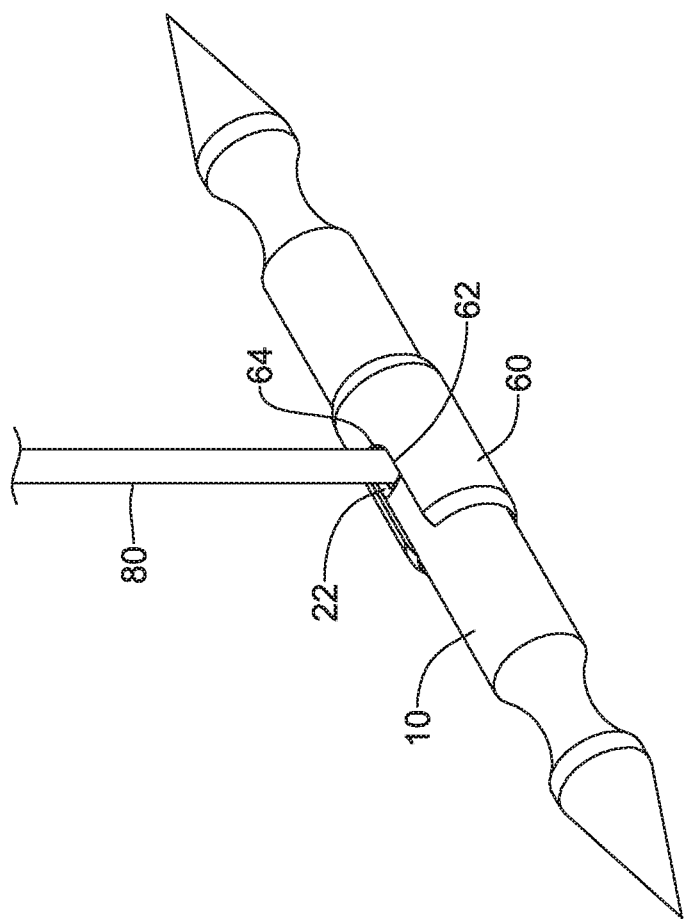

ENDOSCOPIC SUTURING NEEDLE AND SUTURE ASSEMBLY ATTACHMENT METHODS

CROSS-REFERENCE TO RELATED APPLICATIONS

This application claims the benefit of priority under 35 U.S.C. § 119 of U.S. Provisional Application No. 62/848,885 filed May 16, 2019 and U.S. Provisional Application No. 62/727,783, filed Sep. 6, 2018, the entire disclosures of which are hereby incorporated by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for known closure procedures. An assembly including a needle and a suture coupled to the needle may be used to suture tissue together. The tissue attachment method often involves piercing tissue with the needle and pulling on the needle to pull a suture attached to the needle through the hole created in the tissue. One way to couple a suture to a needle involves threading the suture through a hole in the needle and tying a knot at one end of the suture to prevent the end from passing through the hole of the needle. However, knot size can be inconsistent and may, in some examples, pull through the hole in the needle and uncouple the needle and suture, increasing surgical operation times, as operators may need to reassemble the needle and suture. Thus, there is a need for alternative suture and needle assemblies.

SUMMARY

The disclosure is directed to several alternative designs, materials and methods of devices for assembling a needle and suture. In an example, a medical device comprises a needle configured for use in suturing tissue, the needle comprising a cylindrical body extending along a longitudinal axis between first and second ends of the cylindrical body, a lumen extending through the cylindrical body transverse to the longitudinal axis, the lumen having a first opening and a second opening opposite the first opening, and a first end portion at the first end of the cylindrical body, wherein the first end portion includes a first sharp point configured to pierce tissue, wherein an outer surface of the cylindrical body defines a first recess in communication with the first opening of the lumen and configured to receive an end region of a suture, and a sleeve configured to slide over the cylindrical body and compress the end region of the suture within the first recess.

Alternatively or additionally, the sleeve has a slot in an outer wall thereof, the slot sized to receive a portion of the suture extending from the second opening of the lumen.

Alternatively or additionally, the first recess is a first channel extending longitudinally from the first opening of the lumen toward the first sharp point.

Alternatively or additionally, the first channel tapers such that a first end of the first channel adjacent the first opening of the lumen has a first depth that is greater than a second depth at a second end of the first channel opposite the first end of the first channel.

Alternatively or additionally, the outer surface of the cylindrical body defines a second recess in communication with the first opening of the lumen, wherein the second recess is a second channel extending longitudinally from the first opening of the lumen in a direction away from the first sharp point.

Alternatively or additionally, the medical device further comprises a second end portion at the second end of the cylindrical body, wherein the second end portion includes a second sharp point configured to pierce tissue.

Alternatively or additionally, the cylindrical body and the first and second end portions are a single monolithic element.

Alternatively or additionally, the single monolithic element is made of metal.

Alternatively or additionally, the medical device further comprises a depression between the cylindrical body and the first sharp point.

Alternatively or additionally, the medical device further comprises a suture having a first end region including a first terminal end, the first end region extending through the lumen and into the first recess, wherein the first terminal end is disposed within the first recess, wherein the sleeve is disposed over and compresses at least a portion of the first end region within the first recess, and the suture extends from the second opening of the lumen.

Alternatively or additionally, the medical device further comprises a weld fixing the sleeve to the cylindrical body.

Alternatively or additionally, the first end region of the suture is fixed to the cylindrical body with an adhesive or resin.

Alternatively or additionally, the first end region of the suture within the first recess is deformed such that the suture conforms to a shape of the first recess.

Alternatively or additionally, the sleeve is made of a heat shrinkable material.

Alternatively or additionally, the sleeve includes a sharp point configured to pierce tissue.

Alternatively or additionally, the sleeve includes a cavity configured to receive the second end of the cylindrical body.

Alternatively or additionally, the cavity is configured to receive the second end of the cylindrical body in a friction fit.

Alternatively or additionally, the sleeve is configured to be swaged onto the cylindrical body.

Alternatively or additionally, the sleeve is configured to be fixed to the cylindrical body with an adhesive or weld.

In another example, a medical device comprises a needle configured to suture tissue, the needle comprises a cylindrical body extending along a longitudinal axis between first and second ends of the cylindrical body, a slot extending through the cylindrical body transverse to the longitudinal axis, the slot having a first opening and a second opening opposite the first opening, wherein the slot includes a central region configured to receive a suture, the slot including first and second elongated regions extending longitudinally from the central region, and a first end portion at the first end of the cylindrical body, wherein the first end portion includes a sharp point configured to pierce tissue, wherein walls of the cylindrical body along the slot are deformable such that a radially inward force applied to the walls at the central region of the slot causes the walls to deform, thereby compressing and securing the suture received within the central region of the slot.

Alternatively or additionally, the medical device further comprises a second end portion at the second end of the cylindrical body, wherein the second end portion includes a sharp point configured to pierce tissue.

Alternatively or additionally, the cylindrical body and first and second end portions are solid.

Alternatively or additionally, the cylindrical body and first and second end portions are a single monolithic element.

In another example, a medical device comprises a metal needle configured for use in suturing tissue, the metal needle comprising a cylindrical body having a longitudinal axis extending between first and second ends of the cylindrical body, an opening in the cylindrical body transverse to the longitudinal axis, and a first end portion at the first end of the cylindrical body, wherein the first end portion includes a sharp point configured to pierce tissue, and a suture having a coupling member attached to one end, wherein the coupling member is disposed within the opening in the cylindrical body and fixed to the cylindrical body.

Alternatively or additionally, the coupling member is a metal crimp tube crimped onto the suture, and the metal crimp tube is welded to the cylindrical body.

Alternatively or additionally, the coupling member is a wire wrapped around the end of the suture and the wire is fixed to the cylindrical body with adhesive or a weld.

In another example, a medical device comprises a metal needle configured for use in suturing tissue, the metal needle comprising a cylindrical body having a longitudinal axis extending between first and second ends of the cylindrical body, a first lumen extending through the cylindrical body transverse to the longitudinal axis, a second lumen extending through the cylindrical body transverse to the longitudinal axis and transverse to and intersecting the first lumen, and a first end portion at the first end of the cylindrical body, wherein the first end portion includes a sharp point configured to pierce tissue, and first and second fasteners configured to be disposed within the second lumen and configured to compress and fix a suture disposed within the first lumen.

Alternatively or additionally, the first and second fasteners threadingly engage the second lumen.

Alternatively or additionally, the first and second fasteners engage the second lumen with a friction fit.

In another example, a medical device comprises a needle configured for use in suturing tissue, the needle comprising a cylindrical body having a longitudinal axis extending between first and second ends of the cylindrical body, a first end portion at the first end of the cylindrical body, wherein the first end portion includes a sharp point configured to pierce tissue, a cavity in the second end of the cylindrical body, a lumen extending through the cylindrical body, the lumen having a first portion extending transverse to the longitudinal axis, and a second portion extending along the longitudinal axis and in communication with the cavity, and a second end portion with a first end defining a sharp point configured to pierce tissue, and a second end defining a protrusion configured to be received in the cavity of the cylindrical body.

Alternatively or additionally, the protrusion engages the cavity with a friction fit such that when a suture is disposed within the cavity and through the first and second portions of the lumen, the friction fit of the protrusion within the cavity secures the suture to the needle.

Alternatively or additionally, the medical device further comprises a suture disposed within the lumen of the cylindrical body such that a first end of the suture is disposed within the cavity and a second end of the suture extends from the first portion of the lumen, wherein the protrusion is disposed within the cavity and welded to the cylindrical body thereby securing the suture.

In another example, a medical device comprises a metal needle configured for use in suturing tissue, the metal needle comprising a cylindrical body having a longitudinal axis extending between first and second ends of the cylindrical body, first and second end portions at opposite ends of the cylindrical body, wherein the first and second end portions each include a sharp point configured to pierce tissue, at least a first lumen extending through the cylindrical body transverse to the longitudinal axis, and a suture extending through the first lumen, the suture fixed to the cylindrical body.

Alternatively or additionally, the medical device further comprises a second lumen extending through the cylindrical body transverse to the longitudinal axis, wherein the first and second lumens are spaced apart longitudinally.

Alternatively or additionally, the suture extends through the first lumen in a first direction, across the cylindrical body and through the second lumen in a second direction opposite the first direction, wherein the suture is fixed to the cylindrical body.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which:

FIG. 4 is a perspective view of a sleeve forming part of the illustrative suture assembly of FIG. 1;

FIG. 5 is a cross-sectional view of the suture assembly of FIG. 1, taken along the line 5-5;

FIG. 6 is a perspective bottom view of the illustrative suture assembly of FIG. 1;

Figure 1:
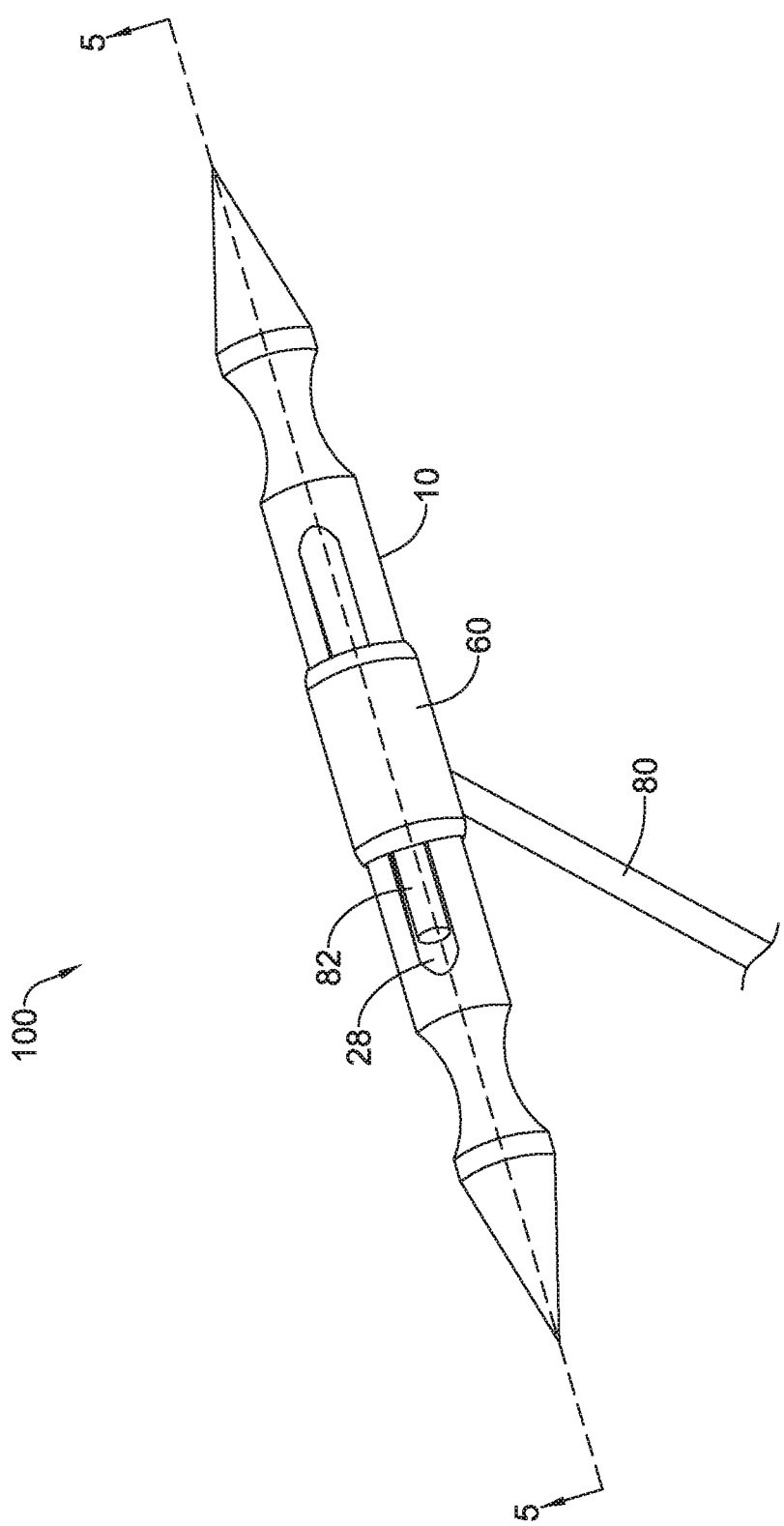
FIG. 1 is a perspective view of an illustrative suture assembly in accordance with an example of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise. As used in this specification and the appended claims, the terms "approximately" and "substantially" may indicate a range of values within +/−5% of a stated value or position.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to needles and suture assemblies that are configured to be used in combination with an endoscope or a similar delivery device for closing wounds within the body. In some instances, the needles and suture assemblies described herein may be configured such that they may be used with a suture based closure device such as that described in U.S. Patent Publication No. 2018/0235604, the entire contents of which are incorporated herein by reference.

FIG. 1 is a perspective view of an exemplary suture assembly 100 including a needle 10, sleeve 60, and suture 80. The needle 10 may include a recess 28 in an outer surface configured to receive a first end region 82 of the suture 80. The suture 80 may be threaded through a lumen 22 (shown in FIG. 2) to extend substantially transverse to the needle 10 as illustrated in FIG. 1. The sleeve 60 may slide over the needle 10 and compress the first end region 82 of the suture 80 within the recess 28.

Figure 2:
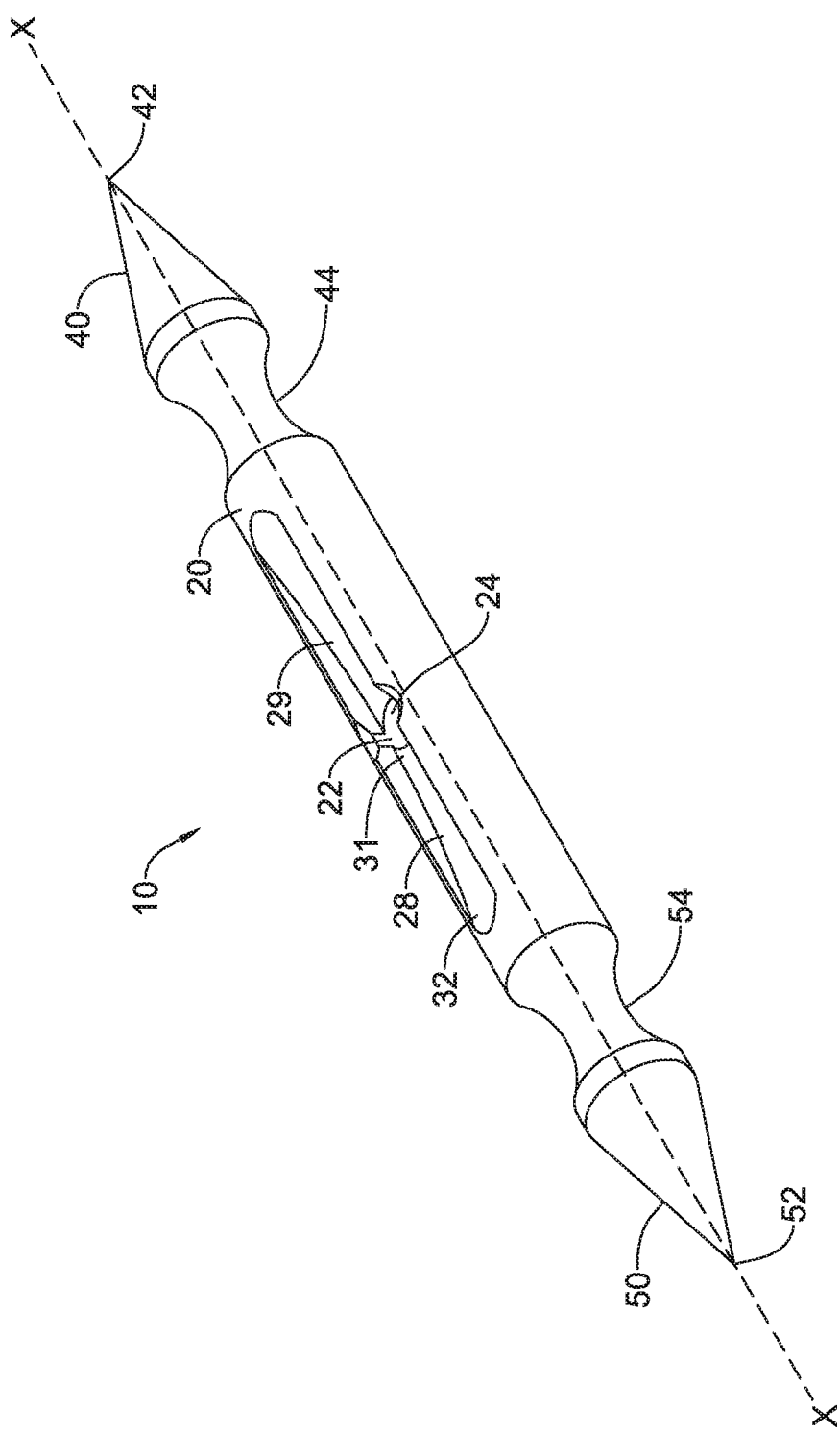
FIG. 2 is a perspective top view of a needle forming part of the illustrative suture assembly of FIG. 1.

As shown in FIG. 2, the needle 10 may have a cylindrical body 20 with a longitudinal axis X-X, a first end portion 40 with a first sharp point 42, and a second end portion 50 with a second sharp point 52. The first and second sharp points 42, 52 are configured to pierce tissue such that the needle 10 may be used to suture tissue. In some examples, the needle 10 may include only the cylindrical body 20 and the first end portion 40 and only a single sharp point 42. In such an example, the opposing end may be blunt. One or both of the first end portion 40 and second end portion 50 may include a depression 44, 54. The depressions 44, 54 may have a curved outer surface that may curve radially inward relative to the longitudinal axis of needle 10. In some examples, depressions 44, 54 may be concavities with a curved exterior surface that may meet and be flush with cylindrical body 20 at an end of the curved surface. In some examples, depressions 44, 54 may be hour-glass shaped and may have an exterior surface that curves radially-inward relative to the exterior surface of cylindrical body 20. In some examples, depressions 44, 54 may be equidistant from a lumen 22 of cylindrical body 20. In some examples, each depression 44, 54 may be configured to receive a bearing ball or other releasable securement member from a medical device. The region of each of the first and second end portions 40, 50 on the opposite end of each sharp point 42, 52, may be coupled to the cylindrical body 20. In some examples, first and second end portions 40, 50 may be attached to cylindrical body 20 by welding, soldering, swaging, or with adhesive. In other examples, the cylindrical body 20, and first and second end portions 40, 50 may be formed as a single monolithic piece.

Needle 10 may also include a lumen 22 extending through cylindrical body 20 transverse to the longitudinal axis X-X. Lumen 22 may extend through a central portion of cylindrical body 20 and may extend substantially perpendicular to the longitudinal axis X-X of cylindrical body 20, as shown in FIG. 2. In other examples, lumen 22 may extend through a non-central portion of cylindrical body 20 and/or be at an angle transverse to the longitudinal axis, but not perpendicular. Lumen 22 may include a first opening 24 on one side of cylindrical body 20 and a second opening 26 (shown in FIG. 3) on the opposite side of cylindrical body 20 from the first opening 24. In some examples, cylindrical body 20 may include at least a first recess 28 extending longitudinally from the lumen 22 on a radially-outer surface of cylindrical body 20. In some examples, first and second recesses 28, 29 may extend from opposite sides of the lumen 22. In some examples, the recess 28 is a channel that tapers such that a first end 31 of the recess 28 adjacent the first opening 24 of the lumen 22 has a first depth that is greater than a second depth at a second end 32 of the recess 28 opposite the first end 31. When present, second recess 29 may be tapered in a similar manner as recess 28. First opening 24 of lumen 22 may be positioned within or otherwise in communication with recesses 28, 29. The recesses 28, 29 may be configured to receive a first end region 82 of a suture 80, as shown in FIG. 1.

Figure 3:
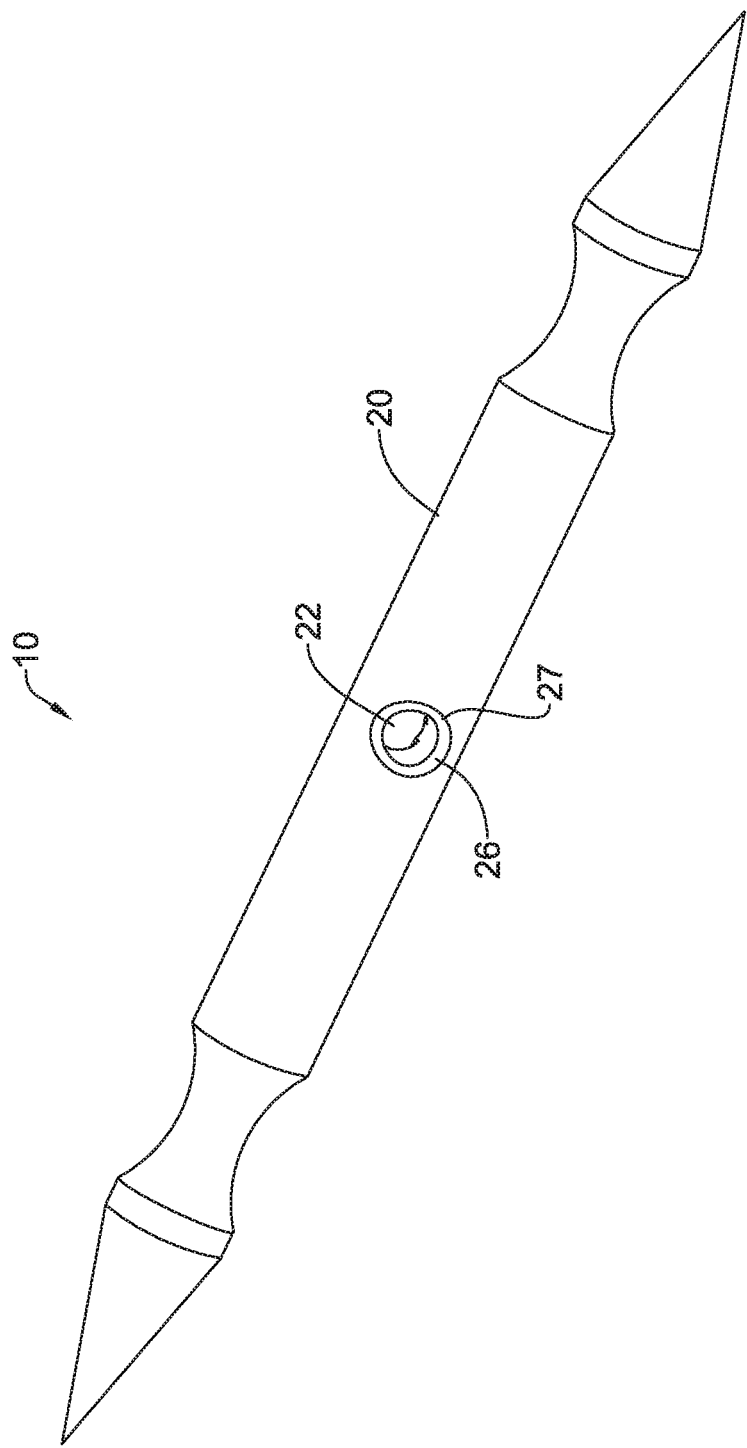
FIG. 3 is a perspective bottom view of the needle of FIG. 2.

FIG. 3 shows the bottom of the needle 10 in FIG. 2. The lumen 22 is shown extending completely through the cylindrical body 20. In some examples, the second opening 26 may include a bevel or counter bore 27. In other examples, the second opening 26 may be flush with the exterior surface of the cylindrical body 20.

FIG. 4 shows the sleeve 60 as a hollow cylinder with two open ends and a slot 62 extending through the sleeve wall in a longitudinal direction from one end towards the middle of the sleeve 60. The slot 62 may have a rounded end 64 configured to engage the suture 80 without damaging or cutting the suture 80.

FIG. 5 is a cross-sectional view of the example suture assembly 100 taken along line 5-5 of FIG. 1. The first end region 82 of the suture 80 is threaded into the second opening 26 and out the first opening 24 of the lumen 22 in the needle 10, and then bent in an L shape such that the first end region 82 and terminal end 84 of the suture 80 reside within the recess 28. Alternatively, the first end region 82 of the suture 80 may reside within recess 29. The sleeve 60 slides over the needle 10 and over the first end region 82 of the suture 80. The recess 28 may have a depth measured transverse to the longitudinal axis that is less than the width of the suture 80, thereby compressing the suture 80 within the recess 28 and securing the suture 80 to the needle 10. The tapered shape of the recess 28 may provide for additional compression of the suture 80.

In some examples, the needle 10 and the sleeve 60 may be metal, and the sleeve 60 may be welded to the needle 10. For example, a weld 90 may be formed between the needle 10 and the sleeve 60 on the bottom of the needle 10, adjacent the second opening 26. In other examples, the sleeve 60 and/or the suture 80 may be fixed to the needle 10 with adhesive or resin. Adhesive or resin may be particularly suitable for fixing the sleeve 60 and/or suture 80 to a needle 10 formed from polymer or other non-metal biocompatible material. In other examples, the sleeve 60 may be made of a heat shrinkable material. The heat shrink sleeve 60 may be slid over the needle 10 and first end region 82 of the suture 80. Heat is then applied causing the heat shrink sleeve 60 to shrink and compress the first end region 82 of the suture 80 within the recess 28. In some examples, the sleeve 60 and the needle 10 may be an interference fit. In some examples, the first end region 82 of the suture 80 may be deformed, e.g., melted, to conform to the shape of the recess 28 to provide additional securement of the suture to the needle 10. With any of the suture securing mechanisms described above, the suture 80 is fixedly coupled to needle 10 such that suture 80 remains within lumen 22 when a pulling force is applied to the suture 80 exiting the second opening 26, such as when using needle 10 to suture a patient.

As shown in FIG. 6, when the sleeve 60 is disposed over the needle 10, the rounded end 64 of the slot 62 engages the suture 80. In some examples, the sleeve 60 may be advanced until the suture 80 is slightly pinched against a side of the lumen 22 and the rounded end 64 of the slot 62.

Figure 7A:
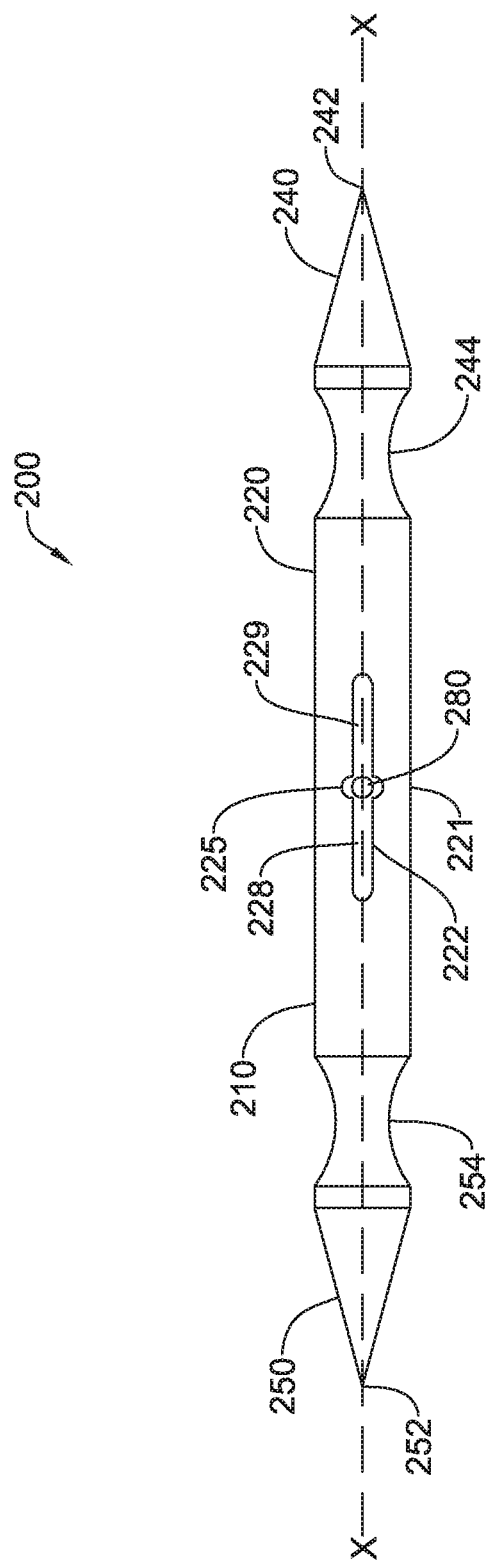
FIG. 7A is a top view of an illustrative suture assembly in accordance with another example of the disclosure, in an open configuration.
Figure 7B:
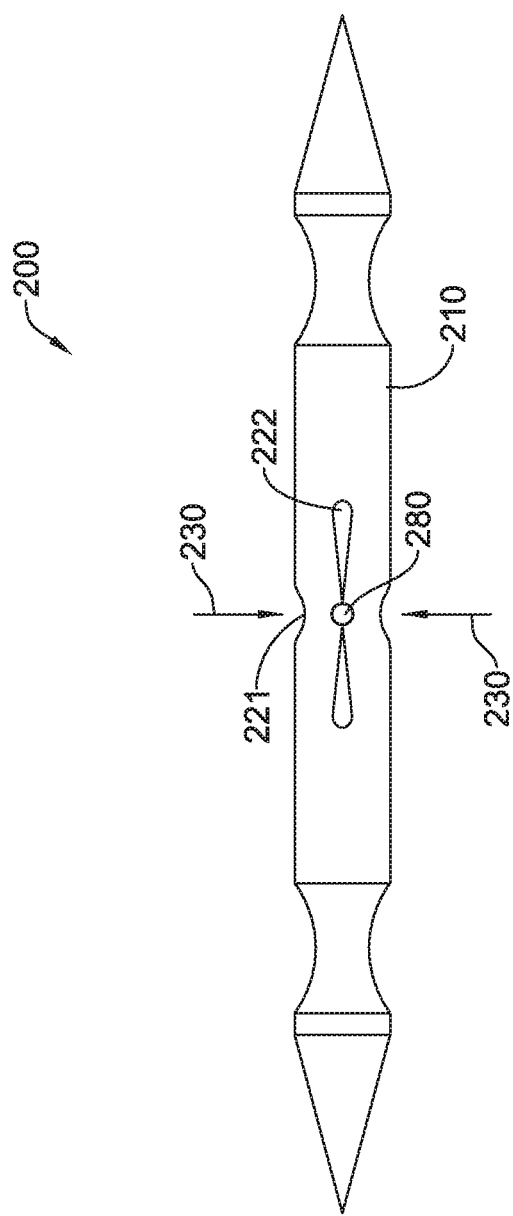
FIG. 7B is a top view of the suture assembly of FIG. 7A in a closed configuration.

FIGS. 7A and 7B illustrate another example suture assembly 200 including a needle 210 and suture 280. FIGS. 7A and 7B show a top or bottom view, with the opposite side being identical. The needle 210 is similar to needle 10, having a cylindrical body 220 and first and second end portions 240, 250, each having a sharp point 242, 252 and a depression 244, 254. The first and second sharp points 242, 252 are configured to pierce tissue such that the needle 210 may be used to suture tissue. The needle 210 may have a slot 222 extending through the cylindrical body 220 transverse to the longitudinal axis X-X, the slot 222 having a first opening on one side of the cylindrical body 220 and a second opening opposite the first opening. The slot 222 may include a central region 225 configured to receive the suture 280, a first elongated region 228, and a second elongated region 229. The first and second elongated regions 228, 229 may extend longitudinally in opposite directions from the central region 225. The central region 225 may have a slightly rounded or semi-circular shape to match the outer shape of the suture 280. The cylindrical body 220 may have walls 221 extending along the slot 222 that are deformable such that a radially inward force applied to the walls 221 in the direction of arrow 230, at the central region 225, causes the walls 221 to deform inwardly where the force is applied, as shown in FIG. 7B. In some examples, once deformed, the walls 221 remain in the deformed configuration shown in FIG. 7B, thereby permanently securing the suture 280 to the needle 210. The walls 221 may be deformed due to their thickness being thinner than a radial thickness of the cylindrical body 220. In other embodiments, the walls 221 may be formed from a material more easily deformed than the remainder of the cylindrical body 220 and/or first and second end portions 240, 250.

Similar to needle 10, the needle 210 may include only the cylindrical body 220 and a single one of the first and second end portions 240, 250 with the sharp point 242, 252. The opposite end may be blunt. In other examples, both the first and second end portions 240, 250 and their respective sharp point 242, 252 may be attached to the cylindrical body. In either case, the cylindrical body 220 may be attached to the first and/or second end portion 240, 250 via welding, soldering, swaging or adhesive. The cylindrical body 220 may be made of the same or a different material from the first and/or second end portions 240, 250. In some examples, the first and/or second end portions 240, 250 are made from a material that is more rigid than the material forming the cylindrical body 220. In other examples, the entire needle 210 including the cylindrical body 220 and first and/or second end portion 240, 250 may be a single monolithic structure. The cylindrical body 220 and the first and/or second end portion 240, 250 may be solid, aside from the slot 222. In some examples, the suture 280 may include a knot or deformed (e.g., melted) region disposed within the central region 225 of the slot 222 or above the slot 222, adjacent the outer surface of the cylindrical body 220. With any of the suture securing mechanisms described above, the suture 280 is fixedly coupled to needle 210 such that suture 280 remains within the central region 225 of the slot 222 when a pulling force is applied to the suture 280, such as when using needle 210 to suture a patient.

Figure 8:
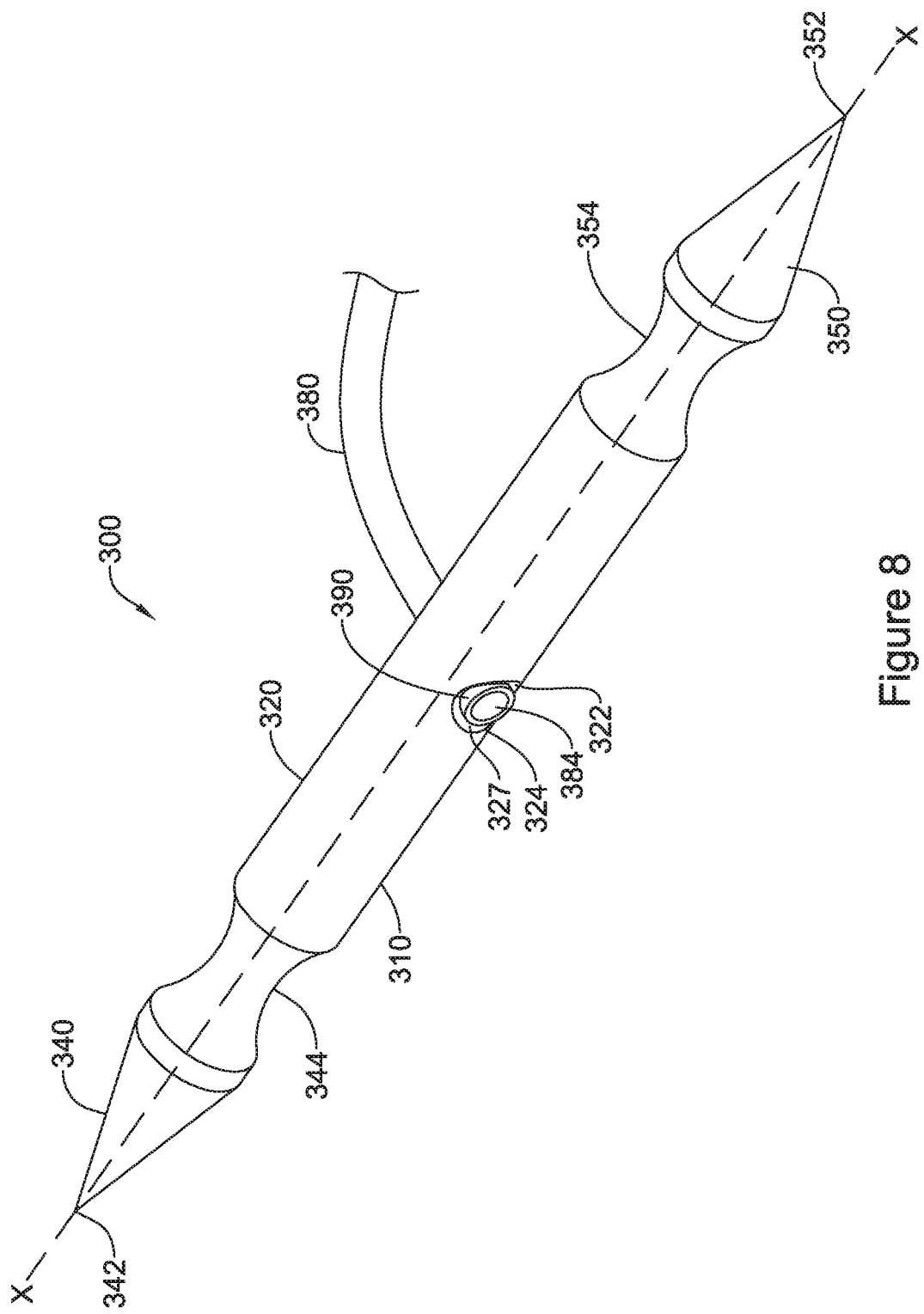
FIG. 8 is a perspective view of an illustrative suture assembly in accordance with another example of the disclosure.
Figure 9:
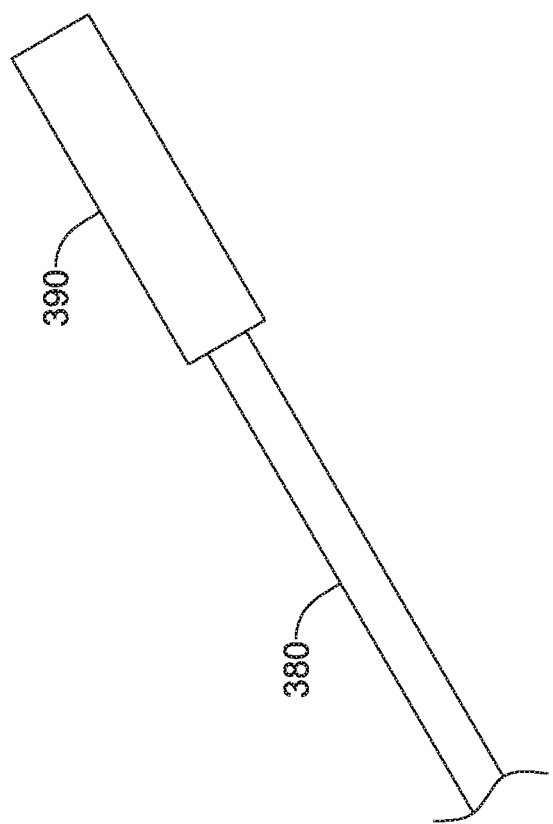
FIG. 9 is a perspective view of the suture and coupling member of FIG. 7.

FIGS. 8 and 9 illustrate another example suture assembly 300 similar to suture assemblies 100 and 200. The suture assembly 300 includes a suture 380 fixed to a needle 310. The needle 310 is similar to needles 10 and 210, having a cylindrical body 320 and first and second end portions 340, 350, each having a sharp point 342, 352 and a depression 344, 354. The first and second sharp points 342, 352 are configured to pierce tissue such that the needle 310 may be used to suture tissue. Needle 310 may also include a lumen 322 extending through cylindrical body 320. Lumen 322 may extend through a central portion of cylindrical body 320 and may extend substantially perpendicular to the longitudinal axis X-X of cylindrical body 320. In other examples, lumen 322 may extend through a non-central portion of cylindrical body 220 and/or be at an angle transverse to the longitudinal axis, but not perpendicular. Lumen 322 may include a first opening 324 on one side of cylindrical body 320 and a second opening (not shown) on the opposite side of cylindrical body 320 from the first opening 324. The first and second openings 324 may be identical. The lumen 322 is shown extending completely through the cylindrical body 320. In some examples, the first, and/or second opening 324 may include a bevel or counter bore 327. In other examples, the first and/or second opening 324 may be flush with the exterior surface of the cylindrical body 320.

Figure 10:
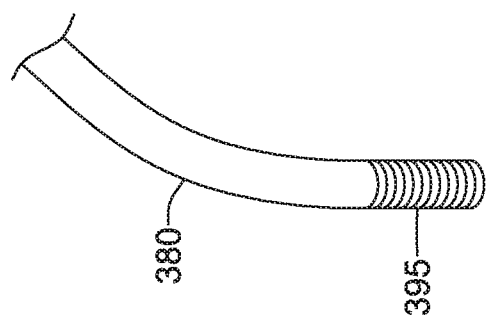
FIG. 10 is a perspective view of an alternative suture and coupling member of FIG. 8.

The suture 380 may include a coupling member 390 fixed adjacent the terminal end 384 of the suture 380. The coupling member 390 may be inserted through the lumen 322 and fixed therein. In the example shown in FIG. 9, the coupling member 390 may be a metal crimp tube. The crimp tube 390 may be placed over the suture 380 and then squeezed or crimped to fix it to the suture 380. The crimp tube 390 may then be inserted into the lumen 322 and fixed therein to secure the suture 380 to the needle 310, as shown in FIG. 8. In some examples, the cylindrical body 320 and the crimp tube 390 may be metal and the crimp tube 390 may be welded or soldered within the lumen 322. In other examples, the crimp tube 390 may be fixed within the lumen 322 with adhesive. FIG. 10 shows an alternative coupling member in the form of a wire 395 wrapped around the suture 380. As with the crimp tube 390, the wire 395 may be welded or soldered within the lumen 322 or fixed with adhesive.

Similar to needle 10, the needle 310 may include only the cylindrical body 320 and a single one of the first or second end portions 340, 350 with the sharp point 342, 352. In some embodiments, the opposite end may be blunt. In other examples, both the first and second end portions 340, 350 and their associated sharp points 342, 352 may be attached to the cylindrical body 320. The cylindrical body 320 may be made of the same or a different material from the first and/or second end portions 340, 350. In some examples, the first and/or second end portions 340, 350 are made from a material that is more rigid than the material forming the cylindrical body 320. In other examples, the entire needle 310 including the cylindrical body 320 and first and/or second end portion 340, 350 may be a single monolithic structure. The cylindrical body 320 and the first and/or second end portion 340, 350 may be solid.

In some examples, the suture 380 may include a knot or deformed (e.g., melted) region disposed within the coupling member 390 or above the coupling member 390, adjacent the outer surface of the cylindrical body 320. With any of the suture securing mechanisms described above, the suture 380 is fixedly coupled to needle 310 such that suture 380 remains within lumen 322 when a pulling force is applied to the suture 380, such as when using needle 310 to suture a patient.

Figure 11:
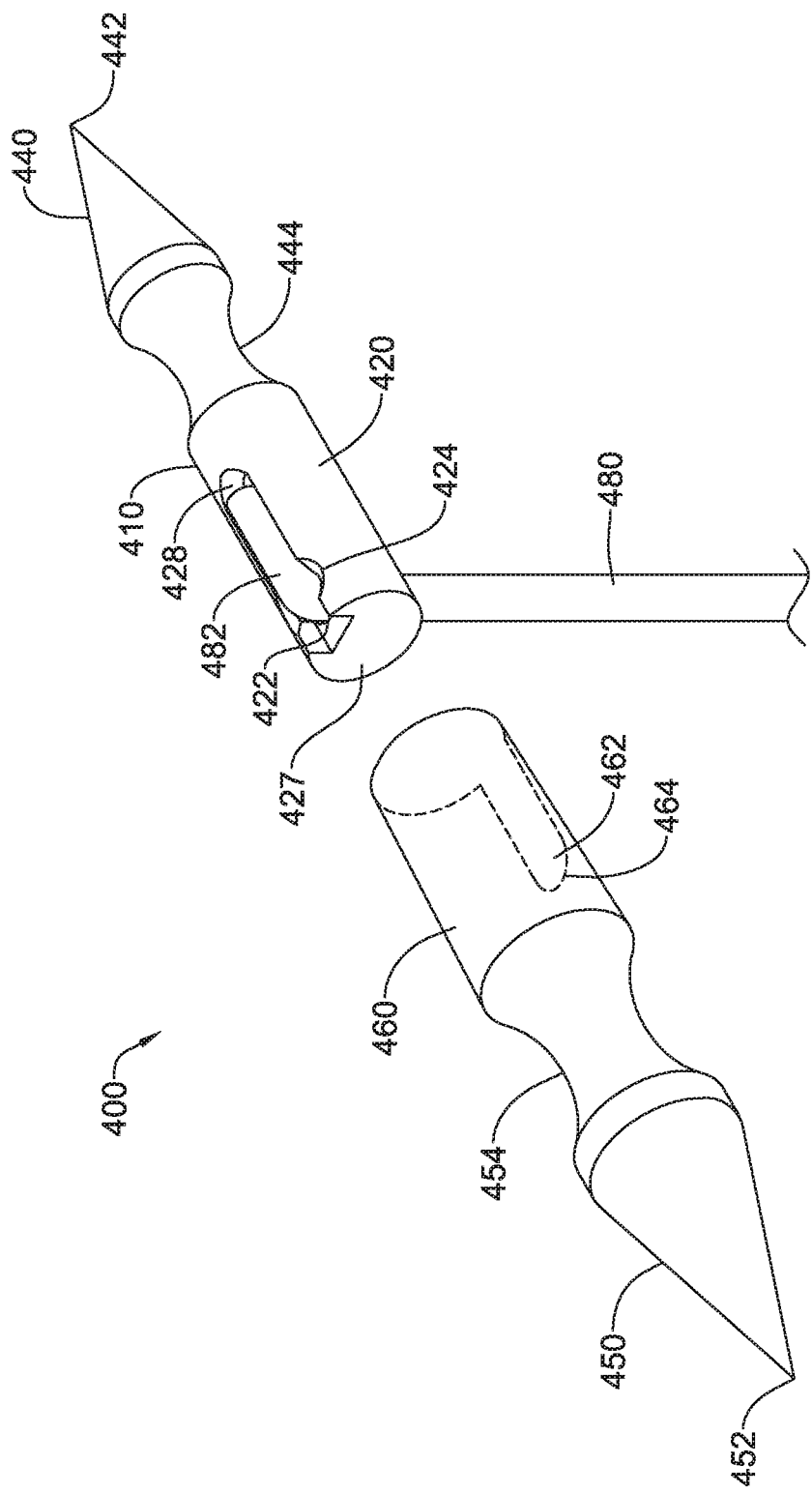
FIG. 11 is a perspective view of an illustrative suture assembly in accordance with another example of the disclosure, in a separated configuration.
Figure 12:
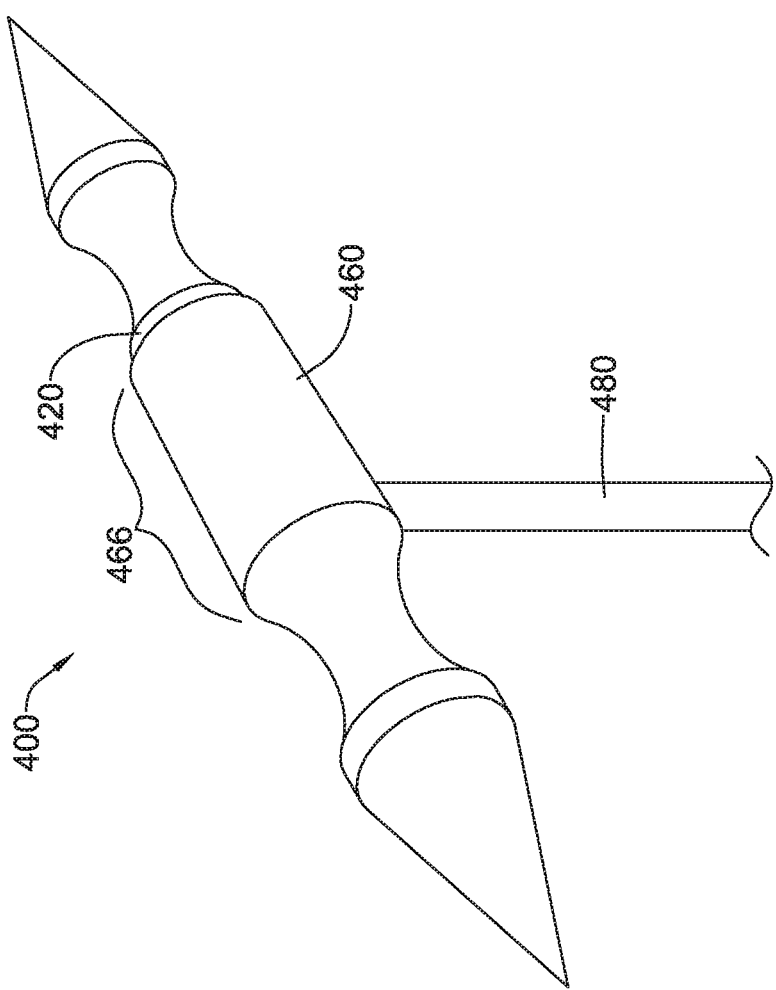
FIG. 12 is a perspective view of the suture assembly of FIG. 11 in a connected configuration.

FIGS. 11 and 12 illustrate another example suture assembly 400 similar to suture assembly 100. The suture assembly 400 includes a suture 480 fixed to a needle 410. The needle 410 is similar to needle 10, having a cylindrical body 420 and first and second end portions 440, 450, each having a sharp point 442, 452 and a depression 444, 454. The first and second sharp points 442, 452 are configured to pierce tissue such that the needle 410 may be used to suture tissue. Needle 410 may also include a lumen 422 extending through cylindrical body 420. Lumen 422 may extend through a central portion of cylindrical body 420 and may extend substantially perpendicular to the longitudinal axis of cylindrical body 420. In other examples, lumen 422 may extend through a non-central portion of cylindrical body 420 and/or be at an angle transverse to the longitudinal axis, but not perpendicular. Lumen 422 may include a first opening 424 on one side of cylindrical body 420 and a second opening (not shown) on the opposite side of cylindrical body 420 from the first opening 424. The lumen 422 may extend completely through the cylindrical body 420.

The cylindrical body 420 may include a recess 428 in an outer surface configured to receive the first end region 482 of the suture 480. The suture 480 may be threaded through the lumen 422 and then the first end region 482 may be bent in an L shape and disposed within the recess 428. The second end portion 450 may include a sleeve portion 460 configured to slide over the cylindrical body 420 and compress the first end region 482 of the suture 480 within the recess 428. The recess 428 may be a channel that tapers as described for recess 28 in needle 10. First opening 424 of lumen 422 may be positioned within or otherwise in communication with recess 428. The sleeve portion 460 of the second end portion 450 may be a hollow cylinder or have a cavity configured to slide over the blunt end 427 of the cylindrical body 420, with a slot 462 extending through the wall in a longitudinal direction from one end towards the middle of the sleeve portion 460. The slot 462 may have a rounded end 464 configured to engage the suture 480 without damaging or cutting the suture 480. The recess 428 may have a depth measured transverse to the longitudinal axis that is less than the width of the suture 480. As the sleeve portion 460 slides over the cylindrical body 420 and over the first end region 482 of the suture 480, the sleeve portion 460 compresses the first end region 482 within the recess 428, thereby securing the suture 480 to the needle 410. The tapered shape of the recess 428 may provide for additional compression of the suture 80.

The sleeve portion 460 may then be swaged onto the cylindrical body 420 to secure the second end portion 450 to the cylindrical body 420. As shown in FIG. 12, the swaged region 466 of the sleeve portion 460 may include substantially the entire length of the sleeve portion 460. In other examples, only an end region of the sleeve portion 460 is swaged onto the cylindrical body 420. Swaging the sleeve portion 460 onto the cylindrical body 420 fixes the suture 480 to the needle 410 such that suture 480 remains within lumen 422 when a pulling force is applied to the suture 480, such as when using needle 410 to suture a patient.

In addition to swaging the sleeve portion 460 onto the cylindrical body 420, in some examples, the sleeve portion 460 may be welded or soldered to the cylindrical body 420. In other examples, adhesive or resin may be used in addition to the swaging, soldering, and/or welding to fix the sleeve portion 460 and/or suture 480 to the needle 410. In other examples, the sleeve portion 460 may be an interference fit with the cylindrical body 420. In other examples, the first end region 482 of the suture 480 may be deformed, e.g., melted, to conform to the shape of the recess 428 to aid in securing the suture to the needle 410.

Figure 13:
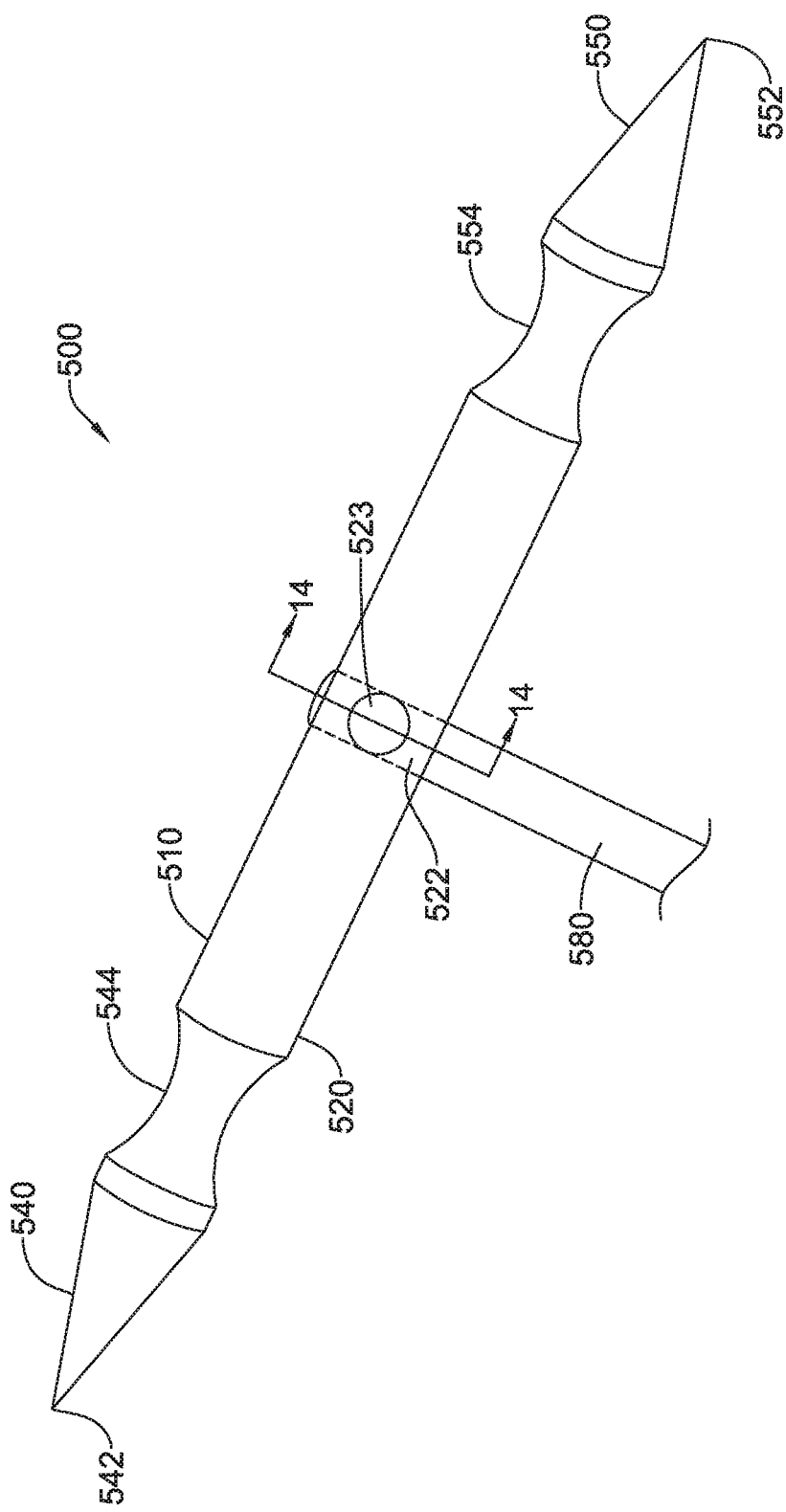
FIG. 13 is a top view of an illustrative suture assembly in accordance with another example of the disclosure.
Figure 14:
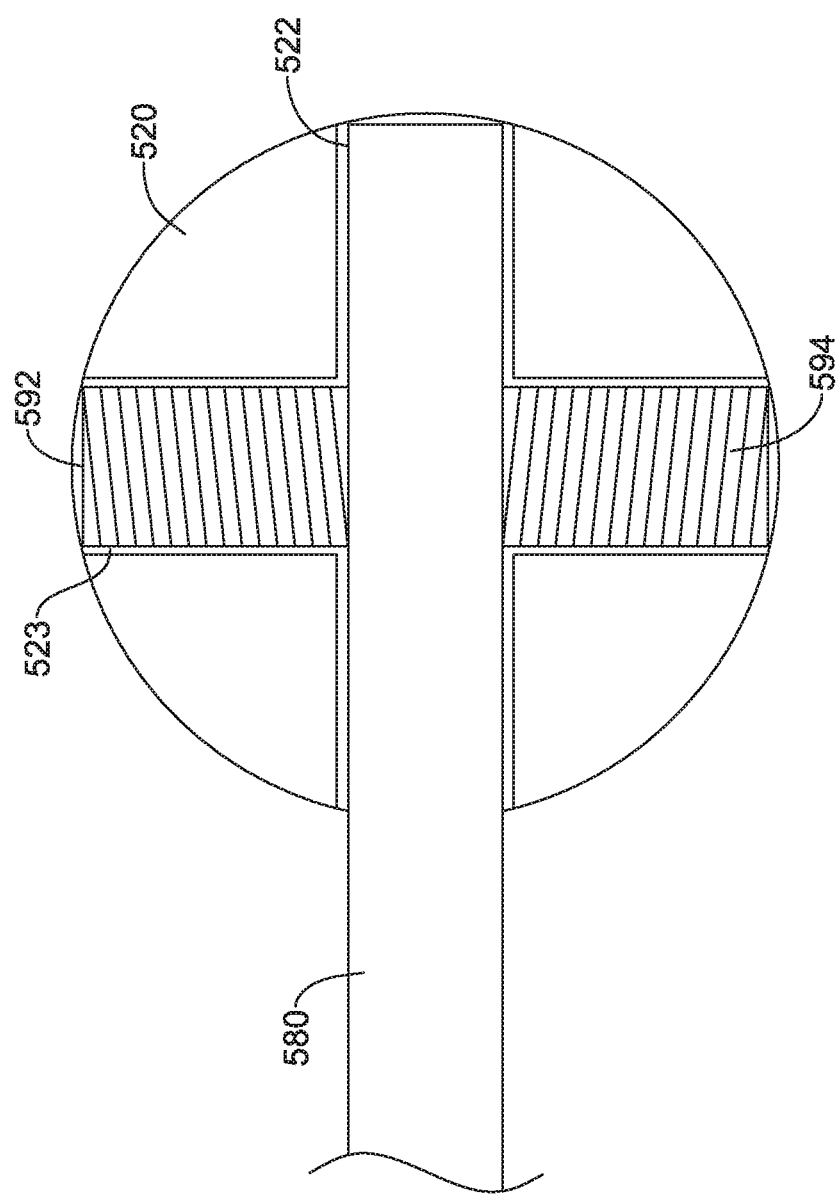
FIG. 14 is a cross-sectional view of the suture assembly of FIG. 13, taken along the line 14-14.

FIGS. 13 and 14 illustrate another example suture assembly 500 similar to suture assemblies 100, 200, 300. The suture assembly 500 includes a suture 580 fixed to a needle 510. The needle 510 is similar to needles 10, 210, 310 having a cylindrical body 520 and first and second end portions 540, 550, each having a sharp point 542, 552 and a depression 544, 554. The first and second sharp points 542, 552 are configured to pierce tissue such that the needle 510 may be used to suture tissue. Needle 510 may also include a first lumen 522 extending through cylindrical body 520.

First lumen 522 may extend through a central portion of cylindrical body 520 and may extend substantially perpendicular to the longitudinal axis of cylindrical body 520. In other examples, first lumen 522 may extend through a non-central portion of cylindrical body 520. The first lumen 522 is shown extending completely through the cylindrical body 520. In some examples, the first lumen 522 may extend only part way through the cylindrical body 520.

A second lumen 523 may extend through the cylindrical body 520 transverse to and intersecting the first lumen 522, as shown in FIG. 14. The suture 580 may be inserted through the first lumen 522. A first fixation member 592 may be inserted through the second lumen 523 from a first direction and a second fixation member 594 may be inserted through the second lumen 523 from a second direction. The first and second fixation members 592, 594 may be advanced until they engage and pinch the suture 580 between them. In some examples, the first and second fixation members 592, 594 may be screws that threadingly engage an internally threaded second lumen 523. In other examples, the first and second fixation members 592, 594 may engage the second lumen 523 with a friction fit. In some examples, the cylindrical body 520 and the first and second fixation members 592, 594 may be metal and the first and second fixation members 592, 594 may be welded or soldered within the second lumen 523. In other examples, the first and second fixation members 592, 594 may be fixed within the second lumen 523 with adhesive.

Similar to needle 10, the needle 510 may include only the cylindrical body 520 and a single one of the first or second end portions 540, 550 with the sharp point 542, 552. The opposite end may be blunt. In other examples, both the first and second end portions 540, 550 and their respective sharp point 542, 552 may be attached to the cylindrical body 520. The first and second sharp points 542, 552 are configured to pierce tissue such that the needle 510 may be used to suture tissue. In either case, the cylindrical body 520 may be attached to the first and/or second end portion 540, 550 via welding, soldering, swaging, or adhesive. The cylindrical body 520 may be made of the same or a different material from the first and/or second end portions 540, 550. In some examples, the first and/or second end portions 540, 550 are made from a material that is more rigid than the material forming the cylindrical body 520. In other examples, the entire needle 510 including the cylindrical body 520 and first and/or second end portion 540, 550 may be a single monolithic structure. The cylindrical body 520 and the first and/or second end portion 540, 550 may be solid.

In some examples, the suture 580 may include a knot or deformed (e.g., melted) region disposed within the first lumen 522 or outside the first lumen 522, adjacent the outer surface of the cylindrical body 520. With any of the suture securing mechanisms described above, the suture 580 is fixedly coupled to needle 510 such that suture 580 remains within the first lumen 522 when a pulling force is applied to the suture 580, such as when using needle 510 to suture a patient.

Figure 15:
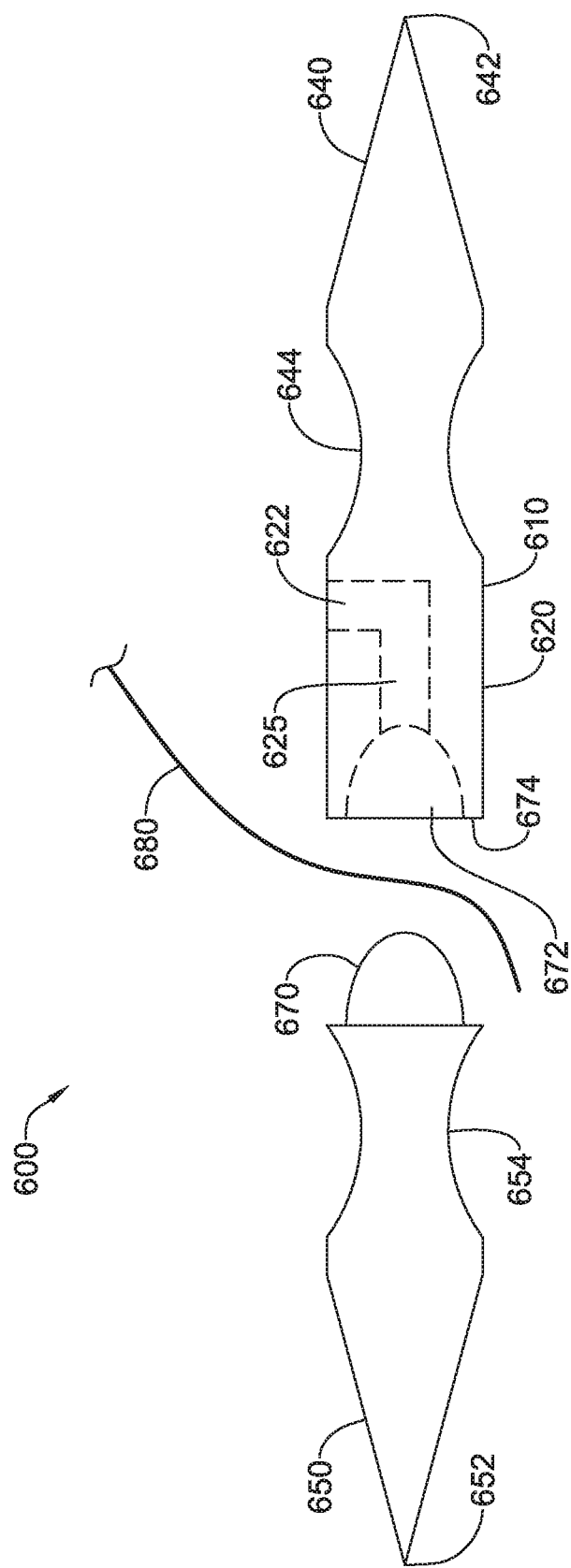
FIG. 15 is a top view of an illustrative suture assembly in accordance with another example of the disclosure, in a separated configuration.
Figure 16:
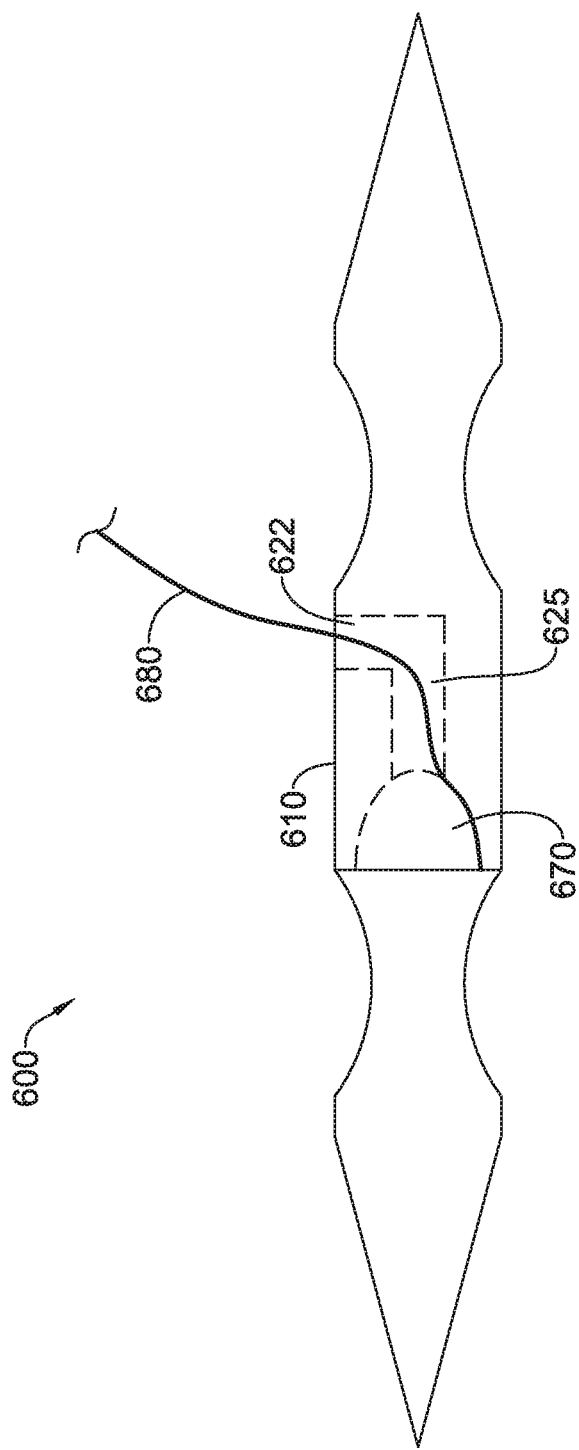
FIG. 16 is a top view of the suture assembly of FIG. 15, in a connected configuration.

FIGS. 15 and 16 illustrate another example suture assembly 600 similar to suture assembly 100. The suture assembly 600 includes a suture 680 fixed to a needle 610. The needle 610 is similar to needle 10, having a cylindrical body 620 and first and second end portions 640, 650, each having a sharp point 642, 652 and a depression 644, 654. The first and second sharp points 642, 652 are configured to pierce tissue such that the needle 610 may be used to suture tissue. Needle 610 may also include a first lumen portion 622 extending part way into cylindrical body 620, as shown by the dashed lines in FIG. 15. First lumen portion 622 may extend into a central portion of cylindrical body 620 and may extend substantially perpendicular to the longitudinal axis of cylindrical body 620. In other examples, first lumen portion 622 may extend through a non-central portion of cylindrical body 620 and/or be at an angle transverse to the longitudinal axis, but not perpendicular. The first lumen portion 622 may intersect a second lumen portion 625 extending longitudinally through the cylindrical body 620. In other examples, the cylindrical body 620 may have a single lumen extending from the cavity 672 to an opening in the wall of the cylindrical body 620 (not shown). The single lumen may be curved or straight.

The cylindrical body 620 may include a cavity 672 in an end face 674 opposite the sharp point 642. The cavity 672 is in communication with the second lumen portion 625 and may be configured to receive a protrusion 670 disposed on an end of the second end portion 650. The protrusion 670 may be received in the cavity 672 with a friction fit. The combination of first and second lumen portions 622, 625 and cavity 672 provide a pathway for the suture 680. The suture 680 may be threaded through the first lumen portion 622, second lumen portion 625, and into the cavity 672. The terminal end of the suture 680 may reside within the cavity 672. As shown in FIG. 16, the protrusion 670 is then inserted into the cavity 672, thereby securing the suture 680 to the needle 610 such that suture 680 remains within the cavity 672 and the first and second lumen portions 622, 625 when a pulling force is applied to the suture 680, such as when using needle 610 to suture a patient.

In addition to the friction fit of the protrusion 670 within the cavity 672, the protrusion 670 may be welded or soldered to the cavity 672 or the end face 674 of the cylindrical body 620. In other examples, the protrusion 670 and/or the suture 680 may be fixed to the needle 610 with adhesive or resin. In other examples, the end region of the suture 680 may be deformed, e.g., melted, to conform to the shape of one or more of the cavity 672, first lumen portion 622, or second lumen portion 625, to aid in securing the suture 680 to the needle 610.

Figure 17:
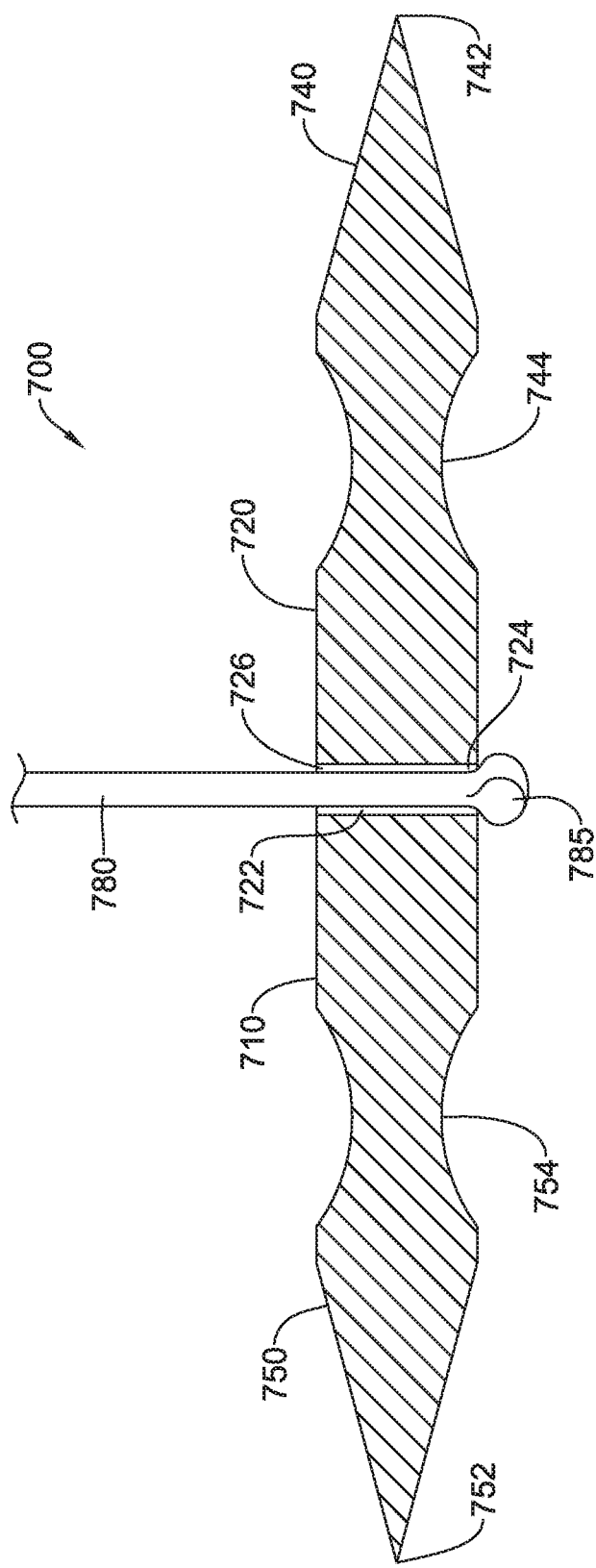
FIG. 17 is a cross-sectional view of an illustrative suture assembly in accordance with another example of the disclosure.
Figure 18:
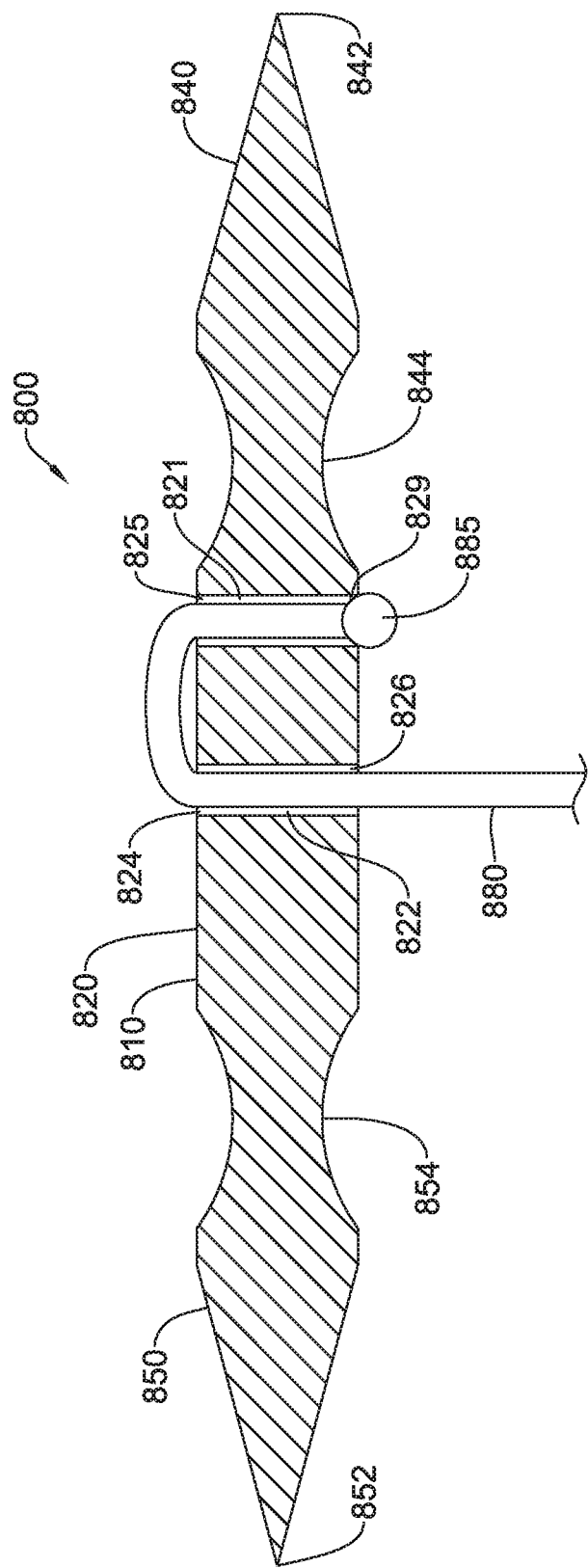
FIG. 18 is a cross-sectional view of an illustrative suture assembly in accordance with another example of the disclosure.

FIGS. 17 and 18 illustrate additional example suture assemblies 700, 800 similar to suture assembly 300. The suture assembly 700 shown in FIG. 17 includes a suture 780 fixed to a needle 710. The needle 710 is similar to needle 310, having a cylindrical body 720 and first and second end portions 740, 750, each having a sharp point 742, 752 and a depression 744, 754. The first and second sharp points 742, 752 are configured to pierce tissue such that the needle 710 may be used to suture tissue. Needle 710 may also include a lumen 722 extending through cylindrical body 720. Lumen 722 may extend through a central portion of cylindrical body 720 and may extend substantially perpendicular to the longitudinal axis of cylindrical body 720. In other examples, lumen 722 may extend through a non-central portion of cylindrical body 720 and/or be at an angle transverse to the longitudinal axis, but not perpendicular. Lumen 722 may include a first opening 724 on one side of cylindrical body 720 and a second opening 726 on the opposite side of cylindrical body 720 from the first opening 724. The first and second openings 724, 726 may be identical. The lumen 722 is shown extending completely through the cylindrical body 720. In some examples, the first, and/or second opening 724, 726 may include a bevel or counter bore as shown in FIG. 8. In other examples, the first and/or second opening 724, 726 may be flush with the exterior surface of the cylindrical body 720 as shown in FIG. 17.

The suture 780 may be inserted through the lumen 722 and a knot 785 tied in the end to prevent the suture 780 from being removed from the lumen 722 through the second opening 726, thereby securing the suture 780 to the needle 710, as shown in FIG. 17. In some embodiments, the suture 780 may have a bulbous end, such that the end 785 is larger than the lumen 722. For example, the bulbous end may be formed by deforming, or melting. In some examples, the suture 780 may be fixed within the lumen 722 with adhesive or adhesive may be added to the knot 785 to secure the knot to the outer surface of the cylindrical body 720.

FIG. 18 shows a suture assembly 800 similar to suture assembly 700 but with a second lumen 821 spaced apart longitudinally from the first lumen 822. The suture assembly 800 shown in FIG. 18 includes a suture 880 fixed to a needle 810. The needle 810 is similar to needle 710, having a cylindrical body 820 and first and second end portions 840, 850, each having a sharp point 842, 852 and a depression 844, 854. The first and second sharp points 842, 852 are configured to pierce tissue such that the needle 810 may be used to suture tissue. Needle 810 includes a first lumen 822 and a second lumen 821 extending through cylindrical body 820. Lumens 822, 821 may extend through a central portion of cylindrical body 820 and may extend substantially perpendicular to the longitudinal axis of cylindrical body 820. In other examples, lumens 822, 821 may extend through a non-central portion of cylindrical body 820 and/or be at an angle transverse to the longitudinal axis, but not perpendicular. Lumens 822, 821 may each include a first opening 824, 825 on one side of cylindrical body 820 and a second opening 826, 829 on the opposite side of cylindrical body 820 from the first opening 824, 825. The first openings 824, 825 and second openings 826, 829 may be identical. The first and second lumens 822, 821 are shown extending completely through the cylindrical body 820. In some examples, the first openings 824, 825, and/or second openings 826, 829 may include a bevel or counter bore as shown in FIG. 8. In other examples, the first and/or second openings may be flush with the exterior surface of the cylindrical body 820 as shown in FIG. 18.

The suture 880 may be inserted through the second opening 826, into the first lumen 822, out the first opening 824 of the first lumen 822, across the outer surface of the cylindrical body 820, into the first opening 825 of the second lumen 821, through the second lumen 821 and out the second opening 829 of the second lumen 821. A knot 885 may be tied in the end to prevent the suture 880 from being removed from the lumens 822, 821 through the second opening 826, thereby securing the suture 880 to the needle 810 such that suture 880 remains within lumens 822, 821 when a pulling force is applied to the suture 880, such as when using needle 810 to suture a patient. In some examples, the suture 880 may be fixed within the first and/or second lumen 822, 821 with adhesive or adhesive may be added to the knot 885 to secure the knot to the cylindrical body 820.

Similar to needle 10, the needles 710, 810 may include only the cylindrical body 720, 820 and a single one of the first end portion 740, 840 or second end portion 750, 850 with its associated sharp point 742, 842, 752, 852. The opposite end may be blunt. In other examples, the needles 710, 810 may include both the first and second end portions 740, 840, 750, 850 and their associated sharp points, as illustrated. In either case, the cylindrical body 720, 820 may be made of the same or a different material from the first and/or second end portions 740, 840, 750, 850. In some examples, the first and/or second end portions 740, 840, 750, 850 are made from a material that is more rigid than the material forming the cylindrical body 720, 820. In other examples, the entire needle 710, 810 including the cylindrical body 720, 820 and first and/or second end portion 740, 840, 750, 850 may be a single monolithic structure.

It will be appreciated that a variety of different materials may be used in forming the devices described herein. The suture 80, 280, 380, 480, 580, 680, 780, 880 may be cylindrical and may be polypropylene. In other examples, the suture may be polyester, nylon, polyglycolic acid, polylactic acid, polymer materials, or any other absorbable or non-absorbable biocompatible material. In some cases, variety of different metals may be used to make the needle 10, 210, 310, 410, 510, 610, 710, 810. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:
1. A medical device comprising:
a needle configured for use in suturing tissue, the needle comprising:
a cylindrical body having a longitudinal axis extending between first and second ends of the cylindrical body;

a lumen extending through the cylindrical body transverse to the longitudinal axis, the lumen having a first opening and a second opening opposite the first opening; and a first end portion at the first end of the cylindrical body, wherein the first end portion includes a first sharp point configured to pierce tissue;

wherein an outer surface of the cylindrical body defines a first recess in communication with the first opening of the lumen and configured to receive an end region of a suture; and a sleeve with a slot in an outer wall thereof, the slot extending from one end of the sleeve toward a middle region of the sleeve, the slot configured to receive a portion of the suture extending from the second opening of the lumen, the sleeve configured to slide over the cylindrical body and compress the end region of the suture within the first recess.

2. The medical device of claim 1, wherein the first recess is a first channel extending longitudinally from the first opening of the lumen toward the first sharp point.

3. The medical device of claim 2, wherein the first channel tapers such that a first end of the first channel adjacent the first opening of the lumen has a first depth that is greater than a second depth at a second end of the first channel opposite the first end of the first channel.

4. The medical device of claim 2, wherein the outer surface of the cylindrical body defines a second recess in communication with the first opening of the lumen, wherein the second recess is a second channel extending longitudinally from the first opening of the lumen in a direction away from the first sharp point.

5. The medical device of claim 1, further comprising a second end portion at the second end of the cylindrical body, wherein the second end portion includes a second sharp point configured to pierce tissue.

6. The medical device of claim 5, wherein the cylindrical body and the first and second end portions are a single monolithic element.

7. The medical device of claim 1, further comprising a depression between the cylindrical body and the first sharp point.

8. The medical device of claim 1, wherein the sleeve is made of a heat shrinkable material.

9. The medical device of claim 1, wherein the sleeve includes a sharp point configured to pierce tissue.

10. The medical device of claim 9, wherein the sleeve is configured to be swaged onto the cylindrical body.

11. The medical device of claim 9, wherein the sleeve includes a cavity configured to receive the second end of the cylindrical body.

12. A medical device comprising:
a needle configured for use in suturing tissue, the needle comprising:
a cylindrical body having a longitudinal axis extending between first and second ends of the cylindrical body;
a lumen extending through the cylindrical body transverse to the longitudinal axis, the lumen having a first opening and a second opening opposite the first opening; and
a first end portion at the first end of the cylindrical body, wherein the first end portion includes a first sharp point configured to pierce tissue;
wherein an outer surface of the cylindrical body defines a first recess in communication with the first opening of the lumen and configured to receive an end region of a suture;
a sleeve configured to slide over the cylindrical body and compress the end region of the suture within the first recess; and
a suture having a first end region including a first terminal end, the first end region extending through the lumen and into the first recess, wherein the first terminal end is disposed within the first recess, wherein the sleeve is disposed over and compresses at least a portion of the first end region within the first recess, and the suture extends from the second opening of the lumen.

13. The medical device of claim 12, wherein the first end region of the suture is fixed to the cylindrical body with a weld, adhesive, or resin.

14. The medical device of claim 12, wherein the first end region of the suture within the first recess is deformed such that the suture conforms to a shape of the first recess.

* * * * *